United States Patent
Sacks et al.

(10) Patent No.: US 7,128,930 B1
(45) Date of Patent: Oct. 31, 2006

(54) COMPOSITIONS AND METHODS FOR TREATING SEXUAL DYSFUNCTION

(75) Inventors: Meir S. Sacks, 5446 Quarino Rd., Pittsburgh, PA (US) 15217; Knox Van Dyke, Morgantown, WV (US)

(73) Assignee: Meir S. Sacks, Pittsburgh, PA (US)

( * ) Notice: Subject to any disclaimer, the term of this patent is extended or adjusted under 35 U.S.C. 154(b) by 0 days.

(21) Appl. No.: 09/653,794

(22) Filed: Sep. 1, 2000

(51) Int. Cl.
*A61K 9/127* (2006.01)

(52) U.S. Cl. ............ 424/450; 514/474; 514/506; 514/944; 514/967

(58) Field of Classification Search .......... 424/450; 514/561, 937–944, 967, 968, 506, 474
See application file for complete search history.

(56) References Cited

U.S. PATENT DOCUMENTS

| 5,439,938 | A |   | 8/1995  | Snyder et al. |
| 5,595,753 | A | * | 1/1997  | Hechtman |
| 5,773,020 | A |   | 6/1998  | Place et al. |
| 6,007,824 | A | * | 12/1999 | Duckett |
| 6,031,002 | A | * | 2/2000  | Wysor |
| 6,051,555 | A |   | 4/2000  | Hadley |
| 6,071,272 | A |   | 6/2000  | Hoffman et al. |
| 6,139,847 | A | * | 10/2000 | Chobanian |
| 6,180,133 | B1| * | 1/2001  | Quan |
| 6,207,713 | B1| * | 3/2001  | Fossel ............. 514/565 |
| 6,340,480 | B1| * | 1/2002  | Duckett et al. ....... 424/728 |
| 6,476,037 | B1| * | 11/2002 | Wallace .......... 514/252.17 |

FOREIGN PATENT DOCUMENTS

| ES | 2091724     | 11/1996 |
| RU | 2163805     | 3/2001  |
| WO | WO 94/01006 | 1/1994  |
| WO | WO 99/51252 | 10/1999 |
| WO | WO 00/00212 | 1/2000  |

OTHER PUBLICATIONS

Derwent-ACC-No. 1996-171281.*
"New Products", Contemporary Ob/Gyn, Jan. 2001, p. 128.

* cited by examiner

*Primary Examiner*—Gollamudi S. Kishore
(74) *Attorney, Agent, or Firm*—Alan G. Towner, Esq.; Pietragallo, Bosick & Gordon, LLP

(57) ABSTRACT

Methods for treating sexual dysfunction are disclosed. The methods generally comprise the administration of an NO donor and an antioxidant; the active ingredients can be administered topically to the genitals of the patient. The methods allow for localized NO delivery through topical application of the present compounds, while minimizing, if not preventing, damage associated with peroxynitrite formation. Compositions comprising L-arginine, or a derivative thereof and an antioxidant in a pharmaceutical carrier suitable for application to the genitals is also disclosed.

6 Claims, No Drawings

COMPOSITIONS AND METHODS FOR TREATING SEXUAL DYSFUNCTION

FIELD OF THE INVENTION

The present invention is directed to compositions useful in treating sexual dysfunction in both men and women. Methods for using these compositions are also within the scope of the present invention.

BACKGROUND INFORMATION

Sexual dysfunction refers collectively to the failure to achieve any one of the four phases of sexual response—appetite, excitement, orgasm, or resolution. Sexual dysfunction is a widespread problem that affects both males and females. It is estimated that millions of people in the United States alone suffer from sexual dysfunction.

Sexual dysfunction in males is typically manifest by the inability to sustain an erection, the inability to ejaculate and/or the inability to experience orgasm. Erectile dysfunction or impotence is the inability to develop and sustain an erection adequate for intercourse and is estimated to affect millions of men in the United States alone. Erectile dysfunction can result from a number of physiological or psychological factors that cause the blood flow to and from the penis to remain imbalanced, thereby preventing retention of sufficient blood to cause rigid dilation and erection. More specifically, erectile dysfunction can be an "arteriogenic" dysfunction in which there is a physical problem with the blood supply to the penis or leakage from veins in the penis such that sufficient pressure cannot be obtained or maintained; a "neurogenic" dysfunction associated with, for example, nerve damage; or a "psychogenic" dysfunction that results from psychological issues such as anxiety or depression.

Sexual dysfunction affects women as well. As applied to women, the term "sexual dysfunction" generally refers to pain or discomfort during sexual intercourse, diminished vaginal lubrication, delayed vaginal engorgement, increased time for arousal, diminished ability to reach orgasm and/or diminished clitoral sensation. Vaginal dryness due to loss of normal vulvar and vaginal secretions most often occurs in menopausal women, women suffering from an autoimmune disease and women undergoing radiation therapy. For women experiencing these problems, sexual intercourse is painful, if possible at all.

Problems with sexual dysfunction are therefore widespread in both males and females. Because of the stigma and embarrassment associated with sexual dysfunction, these problems often go untreated. Even when these problems are treated, the treatments are often undesirable or ineffective. For example, the treatment of males often involves injection into the penis, penile prostheses and urethral implantation of pharmacological agents. Typical treatments for women include the application of antipruritic ointments and creams, or hormone formulas that can cause clitoral enlargement or other masculinization, or that carry a risk of producing atrophy and thinning of the epithelium. Thus, the available treatments can often lead to problems of their own.

SUMMARY OF THE INVENTION

The present invention relates to compositions and methods for using these compositions to treat sexual dysfunction. The present compositions and methods have application both in treating male and female sexual dysfunction. The methods generally employ administering to the genitals of the patient being treated a composition comprising a nitric oxide (NO) donor or producer in conjunction with an antioxidant. More specifically, the NO donor is L-arginine or derivatives thereof. As will be appreciated, these compounds generate NO in vivo. Nitric oxide is a key vasodilator for blood vessels. Vasodilation leads to increased blood flow to the areas in which the vasodilation is effected.

Stretching of the blood vessels, such as that which occurs during vasodilation, causes the endothelial cell production of superoxide ($O_2^-$) from oxygen. The superoxide chemically reacts with nitric oxide to produce peroxynitrite $(OONO)^-$; this reaction diminishes the concentration of nitric oxide available for vasodilation. In addition, peroxynitrite is a strong oxidizer which can, among other things, cause tissue damage and damage to membrane lipids and DNA of cells. Administration of NO generators, therefore, can result in peroxynitrite generation.

The present compositions and methods minimize peroxynitrite levels in the body by depleting superoxide concentrations and by breaking down peroxynitrate that is formed. This is achieved through the use of an antioxidant. Thus, the present methods allow for localized vasodilation through the topical application of the present compositions, while at the same time minimizing, if not eliminating, the tissue and cellular damage associated with other methods of NO generation.

It is therefore an object of the invention to provide compositions for treating sexual dysfunction in a patient.

It is another object of the invention to treat sexual dysfunction in a patient.

It is another object of the invention to increase blood flow to the genitals, without the generation of significant levels of peroxynitrite.

These and other aspects of the invention will be apparent based upon the following description and appended claims.

DETAILED DESCRIPTION OF THE INVENTION

The present invention is directed to methods for treating sexual dysfunction in a patient comprising topically administering to the genitals of the patient an effective amount of L-arginine or derivatives of L-arginine and an effective amount of an antioxidant. L-arginine, derivatives thereof, and antioxidants are referred to collectively herein as "active ingredients". The active ingredients can be administered at different times or concurrently. Accordingly, the present invention is further directed to a composition comprising L-arginine or derivatives thereof, and an antioxidant.

The term "sexual dysfunction" is used herein in its broadest sense as it applies to both males and females. Generally, the term denotes the inhibition of any one or more of the phases of sexual response including appetite, excitement, orgasm or resolution. In males, sexual dysfunction encompasses, for example, decreased sexual desire, the inability to sustain an erection, the inability to ejaculate and/or the inability to experience orgasm. In females, sexual dysfunction refers, for example, to pain or discomfort during sexual intercourse, diminished vaginal lubrication, delayed vaginal engorgement, increased time for arousal, diminished ability to reach orgasm, and/or diminished clitoral sensation. It will be appreciated that treatment of sexual dysfunction as used herein in reference to both males and females encompasses enhancement of sexual pleasure and stimulation. For example, an orgasmic woman seeking a more pronounced sexual response can be treated according to the present methods. A more pronounced sexual response or enhancement of sexual pleasure includes, but is not limited to, decrease in the amount of foreplay, decrease in the period between orgasms, decrease in the intercourse time required for orgasm, and achievement of multiple orgasms.

The term "patient" as used herein refers generally to both male and female members of the animal kingdom. Because the present methods include inducement of sexual stimulation, they have application in, for example, animal husbandry. The present methods are therefore not limited to applications for humans.

As noted, the active ingredients of the present invention are topically administered to the genitals of the patient. In a male, this includes application to the glans (head) or shaft of the penis. Application of the present compounds to the head portion often provides the greatest effect. Female genitals to which the present compositions can be administered include the vagina, clitoris, clitoral hood, labium anterium, labium posterius, labia majora, and labia minora. Preferably, the present compounds are administered to the clitoral hood.

L-arginine is a natural amino acid that is widely commercially available. "Derivatives of L-arginine" refers collectively to NG-hydroxy-L-arginine; di-, tri-, and tetra-peptides wherein the first amino acid at the amino terminal end is L-arginine or $N^G$-hydroxy-L-arginine; esterified L-arginine or hydroxylated L-arginine; amide derivatives of L-arginine or hydroxylated L-arginine; L-homoarginine; hydroxylated L-homoarginine; ester or amide derivatives of L-homoarginine or hydroxylated L-homoarginine and pharmaceutically acceptable salts of any of the above.

$N^G$-hydroxy-L-arginine is the direct intermediate in the production of NO. Hydroxylated L-arginine is commercially available. For example, L-hydroxyarginine acetate can be obtained from Cayman Chemical.

The peptides of the present invention are typically those having 2, 3 or 4 amino acids. The amino terminal amino acid is L-arginine, $N^G$-hydroxy-L-arginine or an ester of either one. The remaining acids in the peptide can also be L-arginine, hydroxylated L-arginine, or esters thereof, or can be any of the other 19 naturally occurring amino acids or derivatives thereof. Preferred peptides include arginine-lysine, arginine-glycine, and arginine-lysine-aspartic acid; hydroxylated L-arginine can be used in place of L-arginine in the preferred peptides.

Esterified versions of L-arginine or hydroxylated L-arginine are prepared, for example, when a reaction occurs at the carboxyl end of the amino acid with, for example, acid chlorides or anhydrides thereby forming an ester at the carboxyl end. These derivatizations render the amino acid "less charged" at the carboxyl end, since the COOH has been esterified. This allows transfer across cell membranes to occur more easily. Particularly preferred are the methyl ester derivatives of L-arginine, the ethyl ester derivatives of L-arginine, and mixtures thereof, although other ester derivatives are equally within the scope of the invention. Esters of L-arginine are commercially available from Sigma Chemical Co., St. Louis, Mo.

Similarly, the amino end of the amino acid can be derivatized by addition of another functional group thereto.

L-homoarginine and hydroxylated L-homoarginine contain an extra methyl group ($-CH_2-$) in the carbon chain of arginine. Either of these amino acids can be further derivitized to form ester or amide derivatives.

The L-arginine and derivatives of L-arginine used according to the present invention generate nitric oxide (NO). As noted above, NO causes vasodilation, which results in increased blood flow to the area in which the vasodilation is effected. Increased blood flow to the erectile tissue of both males and females serves to treat the sexual dysfunction. For example, blood flow to the corpus cavernosa of the penis allows for erection and also facilitates ejaculation and orgasm. Similarly, application of the present compositions to the clitoris and/or clitoral hood of the female results in increased blood supply leading to engorgement of the clitoris. This serves to heighten sexual arousal, enhance sexual pleasure, and otherwise minimize if not eradicate the symptoms associated with sexual dysfunction. Application of the present compositions to the vagina and external genitalia also results in lubrication sufficient so as to allow pain-free sexual intercourse.

Generation of nitric oxide and the vasodilation that occurs as a result can also ultimately lead to the generation of superoxide molecules. Superoxide combines with NO to produce peroxynitrite. The detrimental effects of this reaction are two-fold: the reaction ties up NO, and therefore minimizes the amount of NO available for vasodilation; and the generation of peroxynitrite causes tissue and cellular damage. The present methods and compositions overcome these detrimental effects by use of an antioxidant. The antioxidant converts the superoxide molecule to hydrogen peroxide and oxygen. In sufficient doses, the antioxidants deplete superoxide and break down any peroxynitrite that does form. Any antioxidant that will deplete superoxide levels and/or break down peroxynitrite is therefore within the scope of the present invention. A preferred antioxidant is L-ascorbate, also known as ascorbic acid or vitamin C, and derivatives thereof. Derivatives of vitamin C such as ester C (the calcium salt of L-ascorbate), dehydro-L-ascorbate, (the oxidized derivative of vitamin C), or ester C of dehydro-L-ascorbate can also be used, as can lipidated derivatives such as ascorbic acid palmitate; these compounds are collectively referred to herein as vitamin C derivatives or ascorbic acid derivatives.

While oral administration and injection of various compounds, including various amino acids, have been taught in the art, there is no teaching of application of L-arginine or derivatives thereof, alone or in combination with an antioxidant, in a topical application. It has therefore been discovered that an effective therapeutic level of a NO producer and an antioxidant can be administered topically to the genitals, and transdermally delivered through the skin into sites where the drug is therapeutically effective without damaging the tissue. Thus, the present invention allows for the localized delivery of an NO producer while at the same time minimizing, if not eliminating, the tissue and cellular damage that normally accompanies NO production.

An effective amount of each of the L-arginine or derivatives thereof and the antioxidant should be used. The effective amount can be that amount of the present composition necessary to bring about the desired amount of blood flow to the erectile tissue, while minimizing peroxynitrite damage to that tissue. "Erectile tissue" refers both to the erectile tissue of either the penis or the clitoris. The amount used should cause blood engorgement without significantly modifying motor or sensory functions. An effective amount can also be that amount needed to alleviate one or more of the symptoms of sexual dysfunction. Alleviating the symptoms of sexual dysfunction denotes a decrease in the inhibition of one or more of the four phases of sexual response noted above (appetite, excitement, orgasm or resolution). Such alleviation is manifest by, for example, increasing sexual desire, enhancing the ability to achieve and maintain an erection, enhancing the ability to ejaculate, enhancing the ability to experience orgasm for both males and females, and promoting vaginal lubrication.

It will be appreciated that the effective amount will vary depending on various factors including the patient to be treated, the sex of the patient, the sexual dysfunction being treated, the severity of the dysfunction, the patient's age and reaction to the treatment, the particular formulation employed, and the like. The determination as to what is an effective amount for each patient is within the skill of those practicing in the art. Generally, the dosage of the present compositions comprises at least about 1 milligram up to about 200 milligrams of active L-arginine or L-arginine derivative per ml of vehicle or carrier and at least about 1 milligram up to about 200 milligrams of active per ml of vehicle for the antioxidant. Higher dosages are also well within the scope of the present invention.

It will be appreciated that the antioxidants according to the present methods and compositions are preferably used in supratherapeutic amounts, that is, the amount necessary to control peroxynitrite formation. Thus, the antioxidant is not used in trace amounts to prevent oxidation of the composition itself or to extend the shelf life of the composition, although it also serves that function; the antioxidant itself contributes to the therapeutic benefit realized by the patient.

The active ingredients for the present composition are preferably contained in a pharmaceutical vehicle or carrier suitable for application to the genitals. It will be appreciated that all not all pharmaceutical carriers are appropriate for application to this sensitive region. The active ingredients are therefore preferably contained in a pharmacologically inert excipient, such as those reported in the "Remington Pharmaceutical Sciences Handbook", which will be familiar to those skilled in the art. The composition should be prepared in any administration form that is suitable for topical and epimucosal application to the body and on skin that is particularly thin and sensitive. For example, the pharmaceutical carrier can be a composition which facilitates application of the NO donor and antioxidant. One such carrier is methylcellulose, such as that sold commercially under the name KY® Jelly. Preferably, the carrier has a near neutral pH. Other examples of suitable carriers include water, silicone, waxes, polyethylene glycol, propylene glycol and sugars, and bases containing white petrolatum, paraffin wax, caprylic diglyceryl succinate, diisopropyl adipate and ethoxydiglycol. The composition can be in numerous forms including gels, ointment, foam, spray, cream, salve, lotion, liquid, emulsions, liposomal solution and other forms prepared by methods known in the art. Preferably, the composition has a viscosity such that it will stay generally on the area to which it is applied. A preferred method of delivery is a liposomal solution. Liposomal solutions can be made using commercially available kits following the manufacturer's instructions and with reference to common practices known in the art such as those discussed in "The National Formulary" or "Remingtons Pharmaceutical Sciences Handbook." A pluronic lecithin organogel (PLO) liposomal solution has been found to be particularly suitable.

It will be understood that while "donor" and "antioxidant" are used in the singular, that more than one NO donor and more than one antioxidant can be used in the present methods and compositions.

The compositions according to the present invention can also include any of various other excipients, such as surfactants, suspending agents, emulsifiers, osmotic enhancers, extenders and diluents, pH modifiers, fragrances, colors, flavors, and other additives. For example, a surfactant can be used to enhance the bioavailability of the active ingredients by reducing the tension between these ingredients and the skin of the genitals. Humectants and emollients can also be used, as can absorption or penetration enhancers or other additives commonly used in topical vehicles. Examples of suitable absorption enhancers include dimethylsulfoxide (DMSO) or its analogues, monoalkyl phosphates and pharmaceutically acceptable salts thereof, polyhydroxyesters, long chain fatty acids, polyhydroxyl alcohols and turpenes. The inactive ingredients in the present compositions should be chemically compatible with the active ingredients and should be of a low irritation potential so as not to irritate the genital area.

A preferred composition according to the present invention comprises mixtures of methyl and ethyl esters of L-arginine and vitamin C in a liposomal carrier.

EXAMPLES

The following examples are intended to illustrate the present invention, and should not be construed as limiting the invention in any way.

Five women, each with various sexual dysfunctions, comprised a test group for the present methods and compositions. Their dysfunctions ranged from the inability to produce any vaginal moisture (this woman having had laproscopic removal of the ovaries approximately three years prior to testing) to women with varying degrees of lack of orgasmic fulfillment. Results were graded on a 0 to 10 basis, as reported by the women, with 0 being no sexual response at all to 10 being an extremely powerful sexual response. Each women was given three compositions: a control (which was a PLO vehicle with no active ingredient); the second comprising the PLO vehicle with esterified L-arginine; and the third comprising the PLO vehicle with esterified L-arginine and a combination of ascorbic acid and ascorbic acid-6-palmitate in a 1:1 ratio. The esterified L-arginine was either the ethyl ester of L-arginine or a combination of the ethyl ester and the methyl ester of L-arginine. Three rounds of testing were conducted, in which the concentrations of active ingredients were increased each time. The ratio of L-arginine to antioxidant was approximately 2:1 for those compositions in which both actives were used in all three rounds. The active or actives were contained in approximately 0.5 ml doses in the PLO carrier. The compositions were formulated according to methods commonly known to those skilled in the art for formulating liposomal solutions.

In the first round of testing, approximately 6 milligrams of esterified L-arginine was used. Three of the women did not feel that their sexual response had changed due to the use of any of the compositions. Of the two other women, one who was able to achieve orgasms in the past and who rated her previous orgasms as a 6 on the above scale, said that she had now achieved a better orgasm which she rated an 8. The other woman, who was unable to produce vaginal moisture and who rated her previous sexual response as 0, said that by using the compositions she was autolubricated, producing her own moisture in the vagina, and she rated her sexual experience a 4 on the scale.

A second round of testing was performed utilizing approximately 12 milligrams of esterified L-arginine. In response to this round of testing, two of the women did not feel there was any significant change in their sexual response. The woman who had previously said that by using the first composition, the strength of her orgasm had increased from a 6 on the scale to an 8, said that her orgasm was of greater intensity and could be rated as a 9 by using the "second round" composition. The woman with the inability to autolubricate, who said that her response to round one of the tests could be rated a 4, now felt that her response was up to a 5. A third woman, who previously had felt there was no change in her sexual experience, reported that she had experienced a better orgasm and increased libido based upon use of the stronger composition. She said that her sexual experience that previously numbered a 2 would now rank on the scale as a 5.

In the third round of testing, the concentration of L-arginine was increased to approximately 25 milligrams. In response to the use of this composition, four of the five women reported increases in their sexual experience. The first woman, who had gone from a 6 to an 8 to a 9, reported a response of almost 10 by using the third composition. The woman with the inability to autolubricate who went from 0 to 4 to 5 reported a 10 in response to the third composition. The third woman, who had gone from a 2 to 5 went to about a 6 based upon using the third composition. The fourth woman, who had previously rated her sexual experience at about 1, rated her experience, based upon using the third composition, at a 3.

In all of the rounds of testing, none of the woman reported a response to the control. When an enhanced sexual response was realized, it occurred with the compositions comprising the esterified L-arginine both alone and in combination with the antioxidant; the response based upon use of the composition comprising only the esterified L-arginine was approximately the same as that when using the composition comprising the esterified L-arginine in conjunction with the antioxidant. Cell culturing confirmed that no peroxynitrite, or undetectable levels of peroxynitrite, were present when the composition comprising both the esterified L-arginine and the ascorbic acid combination were used.

As evidenced by the above examples, the present methods are effective in treating sexual dysfunction.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for treating sexual dysfunction in a female patient comprising topically administering to the genitals of said patient an effective amount of esterified L-arginine comprising ethyl ester of L-arginine and an effective amount of an antioxidant said antioxidant is a combination of ascorbic acid and ascorbic acid palmitate.

2. The method of claim 1, wherein said esterified L-arginine and said antioxidant are administered concurrently in the same composition.

3. The method of claim 2, wherein said composition is in the form of a gel, ointment, foam, spray, cream, salve, lotion, liquid, emulsion or liposomal suspension.

4. The method of claim 1, wherein said effective amounts are those amounts necessary to cause the desired level of blood flow to erectile tissue while minimizing peroxynitrite levels.

5. The method of claim 1, wherein said esterified L-arginine and said antioxidant are applied to the clitoral hood.

6. The method of claim 1, wherein said treatment results in enhancement of sexual pleasure.

* * * * *